(12) United States Patent
Ehlert et al.

(10) Patent No.: US 10,471,302 B1
(45) Date of Patent: Nov. 12, 2019

(54) METHOD AND SYSTEM FOR ADMINISTERING AN ACTIVITY PROGRAM

(71) Applicant: Capsule Technologies, Inc., San Diego, CA (US)

(72) Inventors: Kenneth S. Ehlert, Brooklyn Park, MN (US); Mark R. Pollmann, Brooklyn Park, MN (US)

(73) Assignee: CAPSULE TECHNOLOGIES, INC., San Diego, CA (US)

( * ) Notice: Subject to any disclaimer, the term of this patent is extended or adjusted under 35 U.S.C. 154(b) by 373 days.

(21) Appl. No.: 14/535,895

(22) Filed: Nov. 7, 2014

Related U.S. Application Data

(60) Provisional application No. 61/901,823, filed on Nov. 8, 2013.

(51) Int. Cl.
| | |
|---|---|
| *A63B 24/00* | (2006.01) |
| *G04G 21/02* | (2010.01) |
| *A63B 71/06* | (2006.01) |
| *A61B 5/024* | (2006.01) |
| *A61B 5/145* | (2006.01) |
| *A61B 5/11* | (2006.01) |
| *A61B 5/00* | (2006.01) |

(52) U.S. Cl.
CPC .......... *A63B 24/0062* (2013.01); *A61B 5/024* (2013.01); *A61B 5/1118* (2013.01); *A61B 5/14542* (2013.01); *A61B 5/4866* (2013.01); *A63B 71/0622* (2013.01); *G04G 21/025* (2013.01)

(58) Field of Classification Search
CPC ................................................ A63B 24/0062

USPC ........................................................ 434/247
See application file for complete search history.

(56) References Cited

U.S. PATENT DOCUMENTS

| | | | | |
|---|---|---|---|---|
| 2004/0102931 | A1* | 5/2004 | Ellis | A61B 5/1038 |
| | | | | 702/188 |
| 2007/0074618 | A1 | 4/2007 | Vergo | |
| 2012/0253485 | A1* | 10/2012 | Weast | G06F 1/163 |
| | | | | 700/91 |
| 2013/0191034 | A1* | 7/2013 | Weast | G06F 17/00 |
| | | | | 702/19 |

OTHER PUBLICATIONS

Yang, Jun, "Toward Physical Activity Diary: Motion Recognition Using Simple Acceleration Features with Mobile Phones" IMCE'09, Oct. 23, 2009, Beijing, China; Copyright 2009 ACM 978-1-60558-758—May 9, 2010, pp. 1-9.*

(Continued)

*Primary Examiner* — Robert P Bullington
(74) *Attorney, Agent, or Firm* — Alston & Bird LLP

(57) ABSTRACT

A system and method for administering an activity program. An activity goal for an activity and an activity sub-goal for the activity is established. The activity sub-goal includes an activity performance goal and an activity period, wherein the activity performance goal must be met within an amount of time equal to the activity period. The activity goal includes a repetition requirement, wherein the repetition requirement sets a minimum number of times that a measured activity must meet the activity sub-goal over a given time period. Activity is measured and a determination is made as to whether the measured activity meets the activity sub-goal. If so, a determination is made as to whether the corresponding activity goal has been met.

22 Claims, 10 Drawing Sheets

(56) References Cited

OTHER PUBLICATIONS

Carlijn V. C. Bouten, "A Triaxial Accelerometer and Portable Data Processing Unit for the Assessment of Daily Physical Activity" IEEE Transactions on Biomedical Engineering, vol. 44, No. 3, Mar. 1997, pp. 136-147.*

* cited by examiner

| | ACTIVITY PERIOD | ACTIVITY PERF GOAL | TIME PERIOD | SUB-GOALS/ TIME PERIOD | MINIMUM REST PERIOD | REWARD |
|---|---|---|---|---|---|---|
| GOAL 1 | 5 MINS | 300 STEPS | 1 DAY | 5 | 1 HOUR | 1 POINT |
| GOAL 2 | 30 MINS | 3000 STEPS | 1 DAY | 1 | N/A | 1 POINT |
| GOAL 3 | 1 DAY | 10000 STEPS | 1 DAY | 1 | N/A | 1 POINT |

*FIG. 4A*

| | ACTIVITY PERIOD | ACTIVITY PERF GOAL | TIME PERIOD | SUB-GOALS/ TIME PERIOD | MINIMUM INTERVAL | REWARD |
|---|---|---|---|---|---|---|
| GOAL 1 | 1 HOUR | 100 CALORIES | 12 HOURS | 2 | 3 HOURS | NONE |
| GOAL 2 | 10 MINS | 1 MILE | 12 HOURS | 3 | N/A | NONE |

*FIG. 4B*

| | ACTIVITY PERIOD | ACTIVITY PERF GOAL | TIME PERIOD | SUB-GOALS/ TIME PERIOD | MINIMUM REST PERIOD | REWARD |
|---|---|---|---|---|---|---|
| GOAL 1 | 1 HOUR | 3 MILES | 1 WEEK | 5 | 16 HOURS | $14 |
| GOAL 2 | 5 MINS | 300 STEPS | 1 DAY | 4 | 1 HOUR | $2 |

FIG. 4C

| | ACTIVITY PERIOD | ACTIVITY PERF GOAL | TIME PERIOD | SUB-GOALS/ TIME PERIOD | MINIMUM REST PERIOD | REWARD |
|---|---|---|---|---|---|---|
| GOAL 1 (BOTH REQUIRED) | 20 MINS | 2000 STEPS | 1 DAY | 1 | 1 HOUR | DISPLAY SMILEY FACE |
| | 10 MINS | 1000 STEPS | 1 DAY | 1 | 1 HOUR | |

FIG. 4D

METHOD AND SYSTEM FOR ADMINISTERING AN ACTIVITY PROGRAM

CROSS-REFERENCE TO RELATED APPLICATIONS

This application claims the benefit and priority under 35 U.S.C. 119 (e) of U.S. Provisional Application No. 61/901,823, filed Nov. 8, 2013, titled "METHOD AND SYSTEM FOR ADMINISTERING AN ACTIVITY PROGRAM".

BACKGROUND

Physical activity has long been recognized as benefiting health. Early exercise guidelines simply recommended a minimum amount of physical activity within a certain time period—typically a certain number of minutes of exercise within a day or week. More recent research suggests that some patterns of physical activity benefit health more than others. In particular, the frequency and intensity of physical activity influence the degree of health benefit. Long periods of inactivity have been linked to poorer health even among individuals who get recommended amounts of exercise. In addition, more intense physical activity is associated with health benefits not found at lower intensities.

It is impractical, if not impossible, for individuals to constantly monitor the frequency, intensity, and total amount of their physical activity without the aid of technology. Over the last few years, small, inexpensive accelerometers have come to be used in an increasing number of devices including activity trackers which measure activity levels of the user. Activity trackers typically include a computer processor and other components to analyze the accelerometer's data output.

Many organizations including employers and insurance companies encourage their members to exercise more. Many of these organizations operate programs to monitor the physical activity of their members and determine whether they are meeting physical activity goals. Members often receive rewards of various kinds if they meet activity goals.

BRIEF DESCRIPTION OF THE DRAWINGS

Embodiments are illustrated by way of example, and not by way of limitation, in the figures of the accompanying drawings in which like reference numerals refer to similar elements.

FIGS. 4A-4D illustrate example activity goals and activity sub-goals in the system of FIG. 1A;

DETAILED DESCRIPTION

In the following description, the following terms are defined as:

Activity—any measure of an individual's movement. Examples of activity measures include steps taken, calories burned, distance traveled, or the sum of the absolute value of accelerometer readings.

Activity threshold—the minimum amount of physical activity exerted within a duration necessary to achieve a sub-goal.

Activity performance goal—the amount of physical activity required to be performed during an activity period to meet the activity goal.

Activity period or duration—an amount of time during which enough activity must occur to meet an activity performance goal or to meet or exceed an activity threshold. Activity periods and durations are not bounded by fixed beginning or end points.

Sub-goal—the combination of an activity performance goal and the amount of time over which the activity must occur.

Interval—the amount of time between two activity periods or durations.

Time period—a period of time with fixed beginning and end points during which a specific number of sub-goals must be achieved in order to meet a goal.

Reward—Anything received conditioned on completion of a goal. A reward may or may not have monetary value. A reward may or may not be tangible.

Computer-readable storage medium—any medium to which a computer can store data or from which a computer can retrieve data. Examples include, but are not limited to, random access memory (RAM), magnetic disks (hard or floppy), optical disks (including compact disks and digital video disks), and magnetic tapes.

As noted above, physical activity has long been recognized as benefiting health. Recent research suggests the frequency and intensity of physical activity influence the degree of health benefit. Furthermore, long periods of inactivity have been linked to poorer health even among individuals who get recommended amounts of exercise. And more intense physical activity is associated with health benefits not found at lower intensities. Thus, we have developed a system and method for administrating an activity program that monitors and encourages not only total activity but also the frequency and intensity of an individual's physical activity over the course of a selected time period (e.g., a day, a week or a month).

Figure 1A:
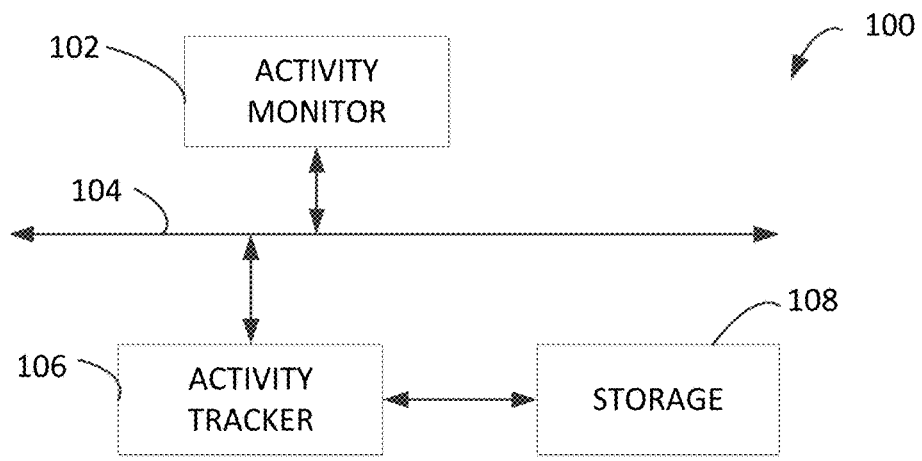
FIGS. 1A and 1B illustrate example embodiments of systems for monitoring physical activity.

FIG. 1A illustrates one embodiment of a system 100 for monitoring physical activity across a population. In the example embodiment of system 100 of FIG. 1, one or more activity monitors 102 capture physical activity on the part of individuals. Monitors 102 report data corresponding to some or all of the captured activity via network 104 to activity tracker 106. Activity tracker 106 processes the data as noted below and stores some or all of the results of the processing in activity data storage 108.

In one embodiment, activity tracker 106 records the frequency, intensity, and total amount of physical activity. In one such embodiment, activity tracker 106 is also used to condition rewards based on data from activity monitor 102.

Figure 1B:
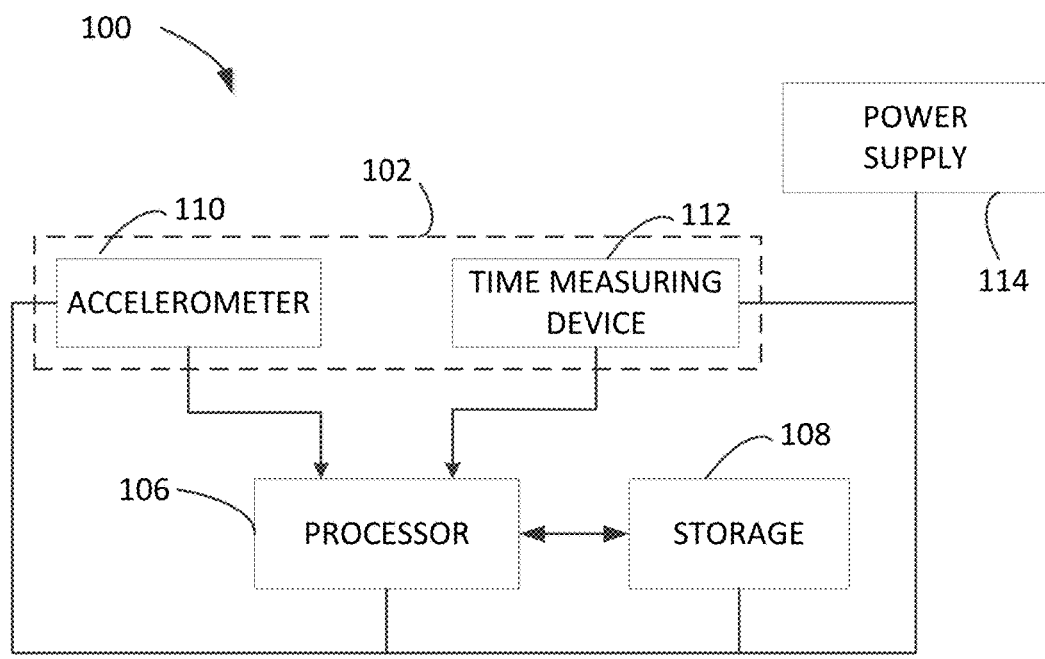

Another example embodiment of a system 100 for assessing physical activity is shown in FIG. 1B. In FIG. 1B, system 100 includes an activity monitor 102, a processor 106 and data storage 108. Processor 106 is connected to activity monitor 102 and receives activity data from activity monitor 102.

In the example embodiment shown in FIG. 1B, activity monitor 102 includes an activity measurement device 110 and a time measuring device 112. In one example embodiment, processor 106 receives data from activity measurement device 102 and from time measuring device 110 and quantifies activity as a function of that data. In the embodiment shown in FIG. 1B, a power supply 114 distributes power to activity measurement device 110, time measuring device 112, processor 106 and data storage 108.

In some embodiments, processor 106 quantifies activity that occurs within activity periods (or durations), compares amounts of activity within the activity periods to activity thresholds, and counts the number of activity periods within which the individual exceeded associated activity thresholds. In one such embodiment, each time the individual meets or exceeds the activity threshold during an activity period counts as meeting a sub-goal; a goal is met by achieving a minimum number of sub-goal over a given time period (e.g., a day).

In some embodiments of the system 100 shown in FIG. 1B, processor 106 quantifies activity that occurs within activity periods, compares amounts of activity within the activity periods to performance activity goals defined for those activity periods, and counts the number of activity periods within which the individual exceeded associated those activity performance goals. In one such embodiment, each time the individual exceeds the activity performance goal during a particular activity period counts as meeting a sub-goal; a goal is met by achieving a minimum number of sub-goal over a given time period (e.g., a day).

In one embodiment, activity measurement device 110 is an accelerometer selected from one of the following: a uniaxial accelerometer, a biaxial accelerometer, or a triaxial accelerometer. In another embodiment, activity measurement device 110 is a 9-axis motion tracking device with a 3-axis angular rate sensor, a 3-axis accelerometer and a 3-axis compass. In another embodiment, activity measurement device 110 is a heart rate monitor. In yet another embodiment, activity measurement device monitors for activity by measuring respiration or other physiological parameters, such as electrodermal activity, galvanic skin response or blood oxygen level (via, for example, pulse oximetry). In one embodiment, activity measurement device 110 includes a GPS sensor.

In one embodiment, time measurement device 110 is selected from one of the following: an electronic quartz crystal clock, a pendulum clock, an atomic clock, a device receiving satellite broadcast of time, or a device counting oscillations in an electrical current.

In one embodiment, processor 106 includes program code for translating activity measurements received from activity measurement device 110 into steps. In one such embodiment, the program code includes program code for estimating steps by counting peaks in accelerometer data that are greater than a specified magnitude.

In one embodiment, processor 106 includes program code for estimating calories burned by calculating an integral of the absolute value of an accelerometer signal.

In one embodiment, processor 106 includes program code for determining whether the number of sub-goals achieved within the time period exceeds a threshold necessary to achieve a goal.

In one embodiment, system 100 includes an accelerometer 110 that transmits acceleration data to processor 106, a time-measuring device 112 that transmits time information electronically to processor 106, a computer readable data storage device 108 connected to the processor 106 for storing accelerometer, data and calculations based thereon, a power supply 114 connected to and providing energy for the accelerometer 110, the time-measuring device 112, the computer-readable data storage 108, and the processor 106. In one such embodiment, processor 106 quantifies activity based on data from the accelerometer, determines the amount of activity within activity periods or durations, compares said quantities of activity to activity thresholds, counts the number of durations within which the individual exceeded associated activity thresholds, each instance of which is the achievement of a sub-goal; and determines whether the number of sub-goals achieved within a time period exceeds a minimum necessary to achieve a goal.

In some embodiments, a method of assessing an individual's physical activity includes determining whether that individual has completed predetermined activity goals. In some embodiments, a goal is completed when an individual has achieved a certain number of sub-goals within a time period. A sub-goal is achieved when the individual exceeds an activity threshold within an associated duration. In some such embodiments, a minimum interval of time must be spent between sub-goals for those sub-goals to be counted toward achievement of the sub-goal. In some embodiments, these minimum intervals define rest periods.

Embodiments can differ as to any of the variables mentioned including the number of goals, the length of durations, the activity threshold for each goal or sub-goal, the number of sub-goals required within each time period, the length of the time period, and the minimum interval between sub-goals.

Figure 2:
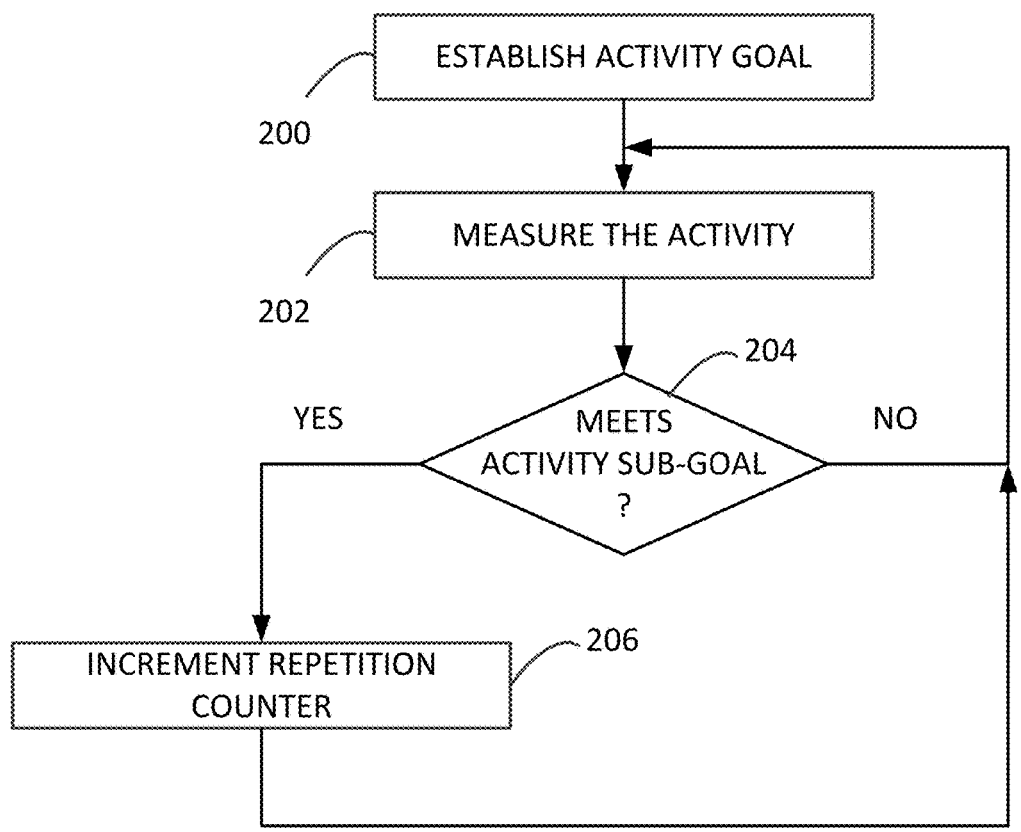
FIG. 2 illustrates a method for tracking activity in the system of FIG. 1A.

A method for tracking activity is shown in FIG. 2. In the example embodiment of FIG. 2, at 200 an activity goal is established. In the embodiment shown in FIG. 2, an activity goal includes one or more activity sub-goals for an activity and the number of times the activity sub-goals must be met to meet the activity goal. Each sub-goal establishes an activity performance goal and an activity period over which the activity performance goal must be met. Some example activity sub-goals are 300 steps over a five minute period and 3000 steps over a thirty minute period. An example activity goal is that the individual must take 300 steps over a five minute period at least five times in a day to meet the activity goal.

After the activity goal with its activity sub-goals is defined at 200, processor 106 begins monitoring, at 202, activity as measured by activity monitor 102. A check is made at 204 to look back and determine if the activity measured has met an activity performance goal for a sub-goal over the last X minutes, where X is the activity period for that particular sub-goal. If not, control moves to 202 and the activity is measured by activity monitor 102. If the activity measured has met an activity performance goal for a sub-goal, a counter is incremented at 206 to count the number of times that particular sub-goal has been met. Control then moves to 202 and the activity is measured by activity monitor 102.

Figure 3:
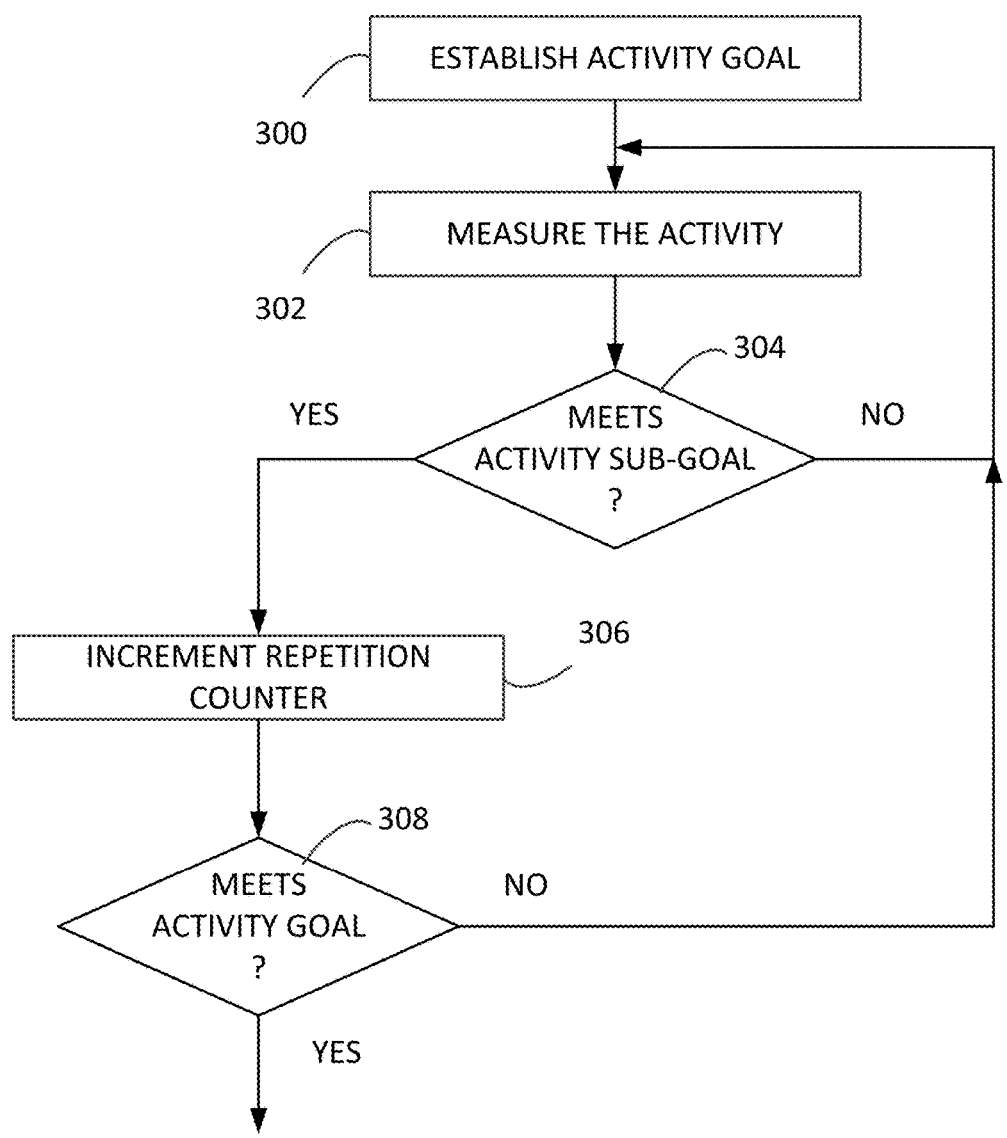
FIG. 3 illustrates another method for tracking activity in the system of FIG. 1A.

Another method for tracking activity is shown in FIG. 3. In the example embodiment of FIG. 3, at 300 an activity goal is established. In the embodiment shown in FIG. 3, an activity goal includes one or more activity sub-goals for an activity and the number of times the activity sub-goals must be met to meet the activity goal. Each sub-goal establishes an activity performance goal and an activity period over which the activity performance goal must be met.

After the activity goal with its activity sub-goals is defined at 300, processor 106 begins monitoring, at 302, activity as measured by activity monitor 102. A check is made at 304 to look back and determine if the activity measured has met an activity performance goal for a sub-goal over the last X minutes, where X is the activity period for that particular sub-goal. If not, control moves to 302 and the activity is measured by activity monitor 102. If the activity measured has met an activity performance goal for a sub-goal, a counter is incremented at 306 to count the number of times that particular sub-goal has been met. Control then moves to 308 and a check is made to see if the number of repetitions required for that sub-goal has been met. If so, the activity is goal has been met. If not, control moves to 302 and the activity is measured by activity monitor 102.

In one embodiment, each activity goal includes a repetition requirement, wherein the repetition requirement sets a minimum number of times that a measured activity must meet the activity sub-goal over a given time period (such as a day, or a week). In one such embodiment, processor 106 maintains a repetition counter for each distinct sub-goal. That repetition counter is incremented each time its corresponding sub-goal is met. Then, the check at 308 to determine if the activity goal has been met includes comparing the contents of the repetition counter to the repetition requirement. In some embodiments, comparing the repetition counter to the repetition requirement includes notifying a user when the repetition requirement is met.

In some embodiments, each activity goal further includes a minimum rest period between activity periods. In some such embodiments, processor 106 notifies a user that the minimum rest period has expired.

In some embodiments, each activity goal further includes a minimum rest period between activity periods and a maximum rest period between activity periods.

In some embodiments, establishing an activity goal includes setting, as the maximum rest period, a maximum wait between activity periods, wherein the method further comprises determining if the maximum rest period has elapsed and, if the maximum rest period has elapsed, encouraging a user to engage in the activity.

In some embodiments, there are two types of activity goals. One type of activity goal includes one or more sub-goals that must be met repeatedly as described above. For that type of activity goal, a repetition requirement is established for each sub-goal, while each sub-goal includes an activity performance goal and an activity period over which the activity performance goal must be met.

The second type of activity goal simply establishes an activity performance goal and an activity period over which the activity performance goal must be met. Examples of each type of activity goal are shown in FIGS. 4A, 4B, 4C and 4D.

In the examples shown in FIGS. 4A and 4B, goal 1 is an activity goal having a single sub-goal. That sub-goal must be met five times for goal 1 in FIG. 4A to be met. The sub-goal must be met twice for goal 1 in FIG. 4B to be met. Goal 2 in FIG. 4B is also an activity goal with a sub-goal that must be met three times in a twelve hour period.

Goals 2 and 3 in FIG. 4A, on the other hand, are activity goals without sub-goals.

Goals 1 and 2 in FIG. 4C are activity goals with single sub-goals. The sub-goal for goal 1 must be met five times for goal 1 to be met while the sub-goal for goal 2 must be met four times for goal 2 to be met.

Finally, goal 1 in FIG. 4D is an activity goal with two different sub-goals. One sub-goal requires 2000 steps over a twenty minute period, while the other requires 1000 steps over a ten minute period. The repetition requirement for each sub-goal in FIG. 4D is set to one.

The example embodiments shown in FIGS. 4A-4D also demonstrate the use of a time period, a minimum rest period and a reward. In some embodiments, the reward is part of the program used to encourage activity within a group of individuals.

In the example embodiment shown in FIG. 4A, system 100 is configured to require three activity goals, each of which must be completed within a time period of one day. The first goal is to take at least 300 steps within each of five 5-minute durations, each of said durations being separated by an interval of at least one hour. The second goal is to take at least 3000 steps within thirty minutes. The third goal is to take at least 10000 steps within the day. For the third goal, the duration and the time period are one and the same. In the embodiment shown in FIG. 4A, achievement of each goal is rewarded with a single point in a point system that, in some embodiments, is part of a competition, and, in other embodiments, is redeemable for value.

In the example embodiment shown in FIG. 4B, system 100 is configured to require two activity goals, each of which must be completed within twelve hours. The first goal is to burn at least 100 calories within each of two 1-hour durations, each of said durations being separated by an interval of at least three hours. The second goal is to run at least one mile within each of two 10-minute durations with no requirement for an interval between each activity period. In the example shown in FIG. 4B, there are no rewards for meeting these goals other than, perhaps, the satisfaction of having completed them.

In the example embodiment shown in FIG. 4C, system 100 is configured to require two activity goals. The first goal is to travel at least three miles within each of five 1-hour periods, each of said periods being separated by an interval of at least twelve hours, with each sub-goal to be completed within the time period of a week. The reward for completing the first goal is $14. The second goal is to take at least 300 steps within each of five 5-minute periods, each of said periods being separated by an interval of at least one hour, with each sub-goal to be completed within a day. The reward for completing the second goal is $2 and there is an opportunity to achieve the second goal on each successive day within the one-week time period of the first goal.

In the example embodiment shown in FIG. 4D, system 100 is configured to require a single activity goal with two different sub-goals necessary to satisfy the activity goal. The first sub-goal is to take at least 2000 steps within a period of 20 minutes. The second component is to take at least 1000 steps within a period of 10 minutes. Each particular sub-goal must be separated from like sub-goals by an interval of at least one hour and both sub-goals must be completed the requisite number of times (once) to achieve the goal. The reward for completing the goal is to see the image of a smiley face on a computer screen.

Figure 5:
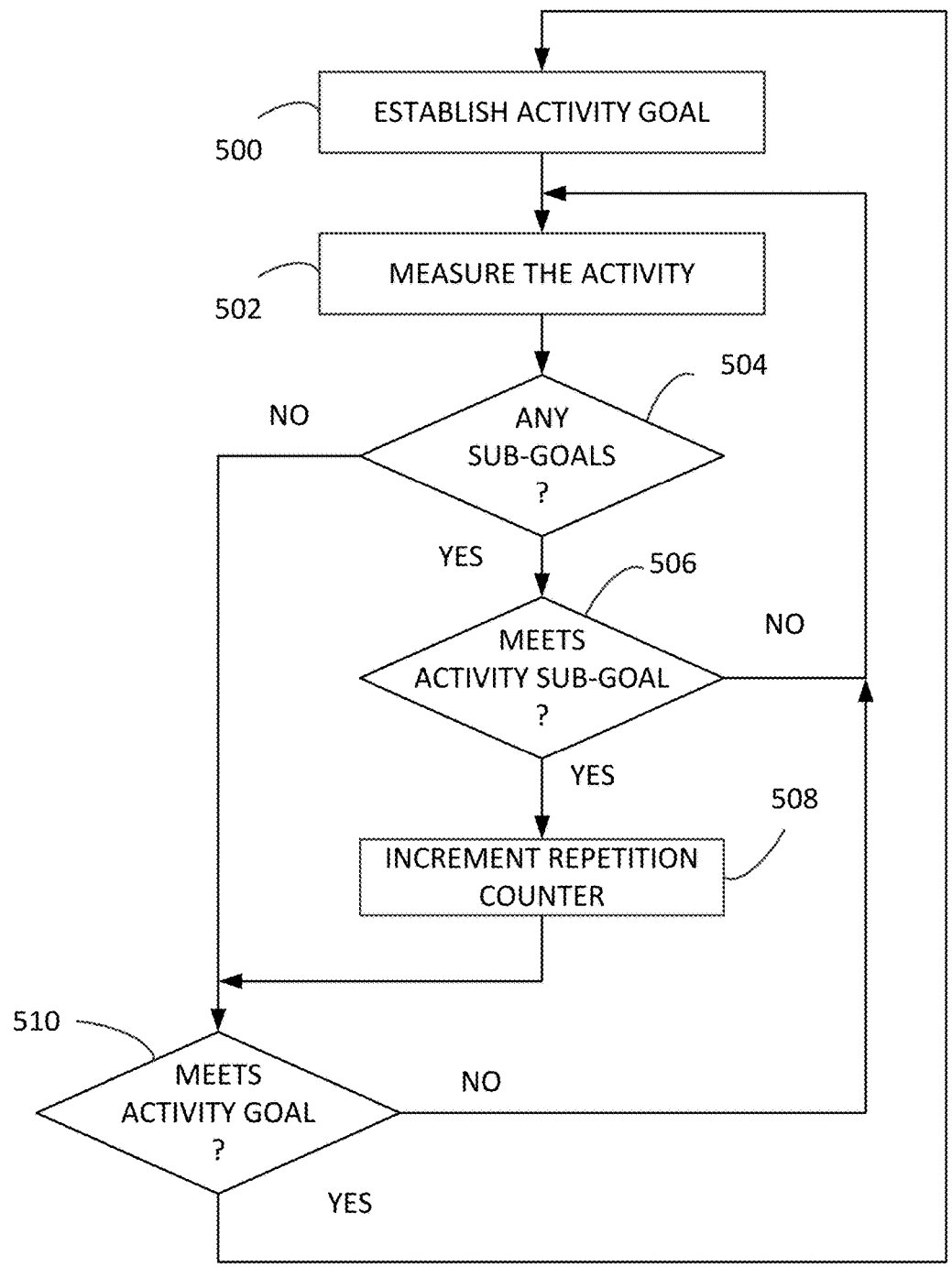
FIG. 5 illustrates yet another method for tracking activity in the system of FIG. 1A.

Another method for tracking activity is shown in FIG. 5. In the example embodiment of FIG. 5, at 500 an activity goal is established. In the embodiment shown in FIG. 5, an activity goal may include one or more activity sub-goals. If there are any sub-goals, the activity goal will also include a repetition requirement that establishes the number of times the activity sub-goals must be met to meet the activity goal. Each sub-goal establishes an activity performance goal and an activity period over which the activity performance goal must be met.

After the activity goal with its activity sub-goals, if any, is defined at 500, processor 106 begins monitoring, at 502, activity as measured by activity monitor 102. A check is made at 504 to see if there are any sub-goals associated with the activity. If not, control moves to 510.

If, however, there are sub-goals associated with the activity, control moves to 506 and processor 106 looks back to determine if the activity measured has met an activity performance goal for one or more of the sub-goals over the last X minutes, where X is the activity period for that particular sub-goal. If not, control moves to 502 and the activity is measured by activity monitor 102.

If, however, the activity measured has met an activity performance goal for a sub-goal, a counter is incremented at 508 to count the number of times that particular sub-goal has been met. Control then moves to 510.

At 510, a check is made to determine if an activity goal has been met. For some activity goals, this requires a check to see if the number of repetitions required for sub-goals of that activity goal have been met. If so, the activity goal has been met. If not, control moves to 502 and the activity is measured by activity monitor 102.

For activity goals without sub-goals, a check is made at 510 to determine if the activity measured has met an activity performance goal over the last X minutes, where X is the activity period for that particular activity goal. If not, control moves to 502 and the activity is measured by activity monitor 102.

In the embodiment described with respect to FIG. 5, each activity goal with sub-goals includes a repetition requirement, wherein the repetition requirement sets a minimum number of times that a measured activity must meet the activity sub-goal over a given time period (such as a day, or a week). In one such embodiment, processor 106 maintains a repetition counter for each distinct sub-goal. That repetition counter is incremented each time its corresponding sub-goal is met. Then, the check at 510 to determine if the activity goal has been met includes comparing the contents of the repetition counter to the repetition requirement. In some embodiments, comparing the repetition counter to the repetition requirement includes notifying a user when the repetition requirement is met.

In some embodiments, each activity goal further includes a minimum rest period between activity periods. In some such embodiments, processor 106 notifies a user that the minimum rest period has expired.

In some embodiments, each activity goal further includes a minimum rest period between activity periods and a maximum rest period between activity periods.

In some embodiments, establishing an activity goal includes setting, as the maximum rest period, a maximum wait between activity periods, wherein the method further comprises determining if the maximum rest period has elapsed and, if the maximum rest period has elapsed, encouraging a user to engage in the activity.

Figure 6:
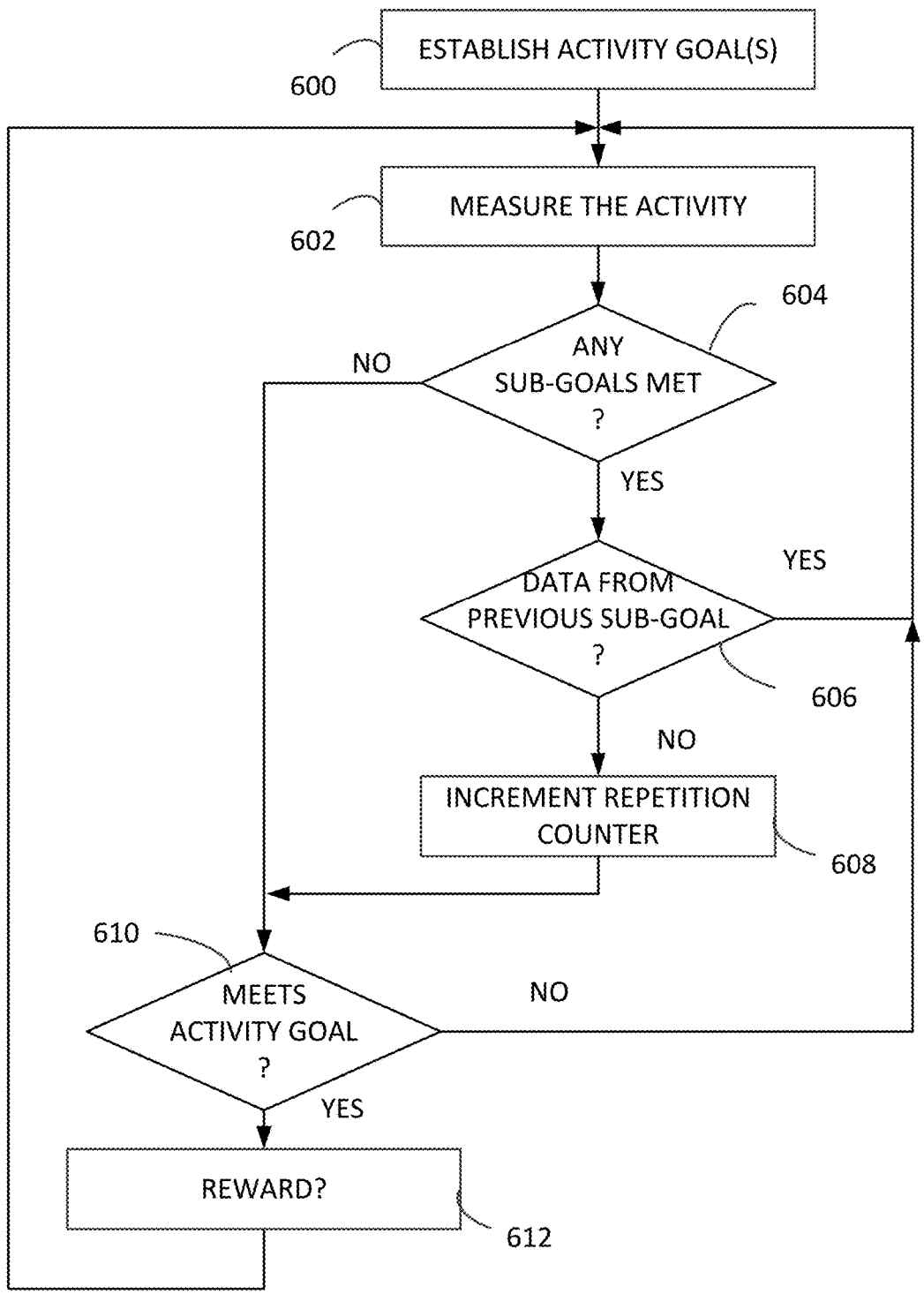
FIG. 6 illustrates yet another method for tracking activity in the system of FIG. 1A.

Yet another method for tracking activity is shown in FIG. 6. In the example embodiment of FIG. 6, at 600, one or more an activity goals is established. In the embodiment shown in FIG. 6, an activity goal may include one or more activity sub-goals. If there are any sub-goals, the activity goal will also include a repetition requirement that establishes the number of times the activity sub-goals must be met to meet the activity goal. Each sub-goal establishes an activity performance goal and an activity period over which the activity performance goal must be met.

After activity goals with their activity sub-goals, if any, are defined at 600, processor 106 begins monitoring, at 602, activity as measured by activity monitor 102. A check is made at 604 to determine if the activity measured has met an activity performance goal for one or more of the sub-goals over the last X minutes, where X is the activity period for that particular sub-goal. If not, control moves to 610.

If, however, the activity measured has met an activity performance goal for a sub-goal, a check is made at 606 to determine if the activity measured over the period includes activity used to meet a previous instance of the same sub-goal. If so, control moves to 602 and activity monitor 102 continues to measure activity. If, however, the activity measured over the period does not include activity used to meet a previous instance of the same sub-goal, a counter is incremented at 608 to count the number of times that particular sub-goal has been met. Control then moves to 610.

At 610, a check is made to determine if an activity goal has been met. For some activity goals, this requires a check to see if the number of repetitions required for each sub-goal of that activity goal have been met. If so, the activity goal has been met. If not, control moves to 602 and the activity is measured by activity monitor 102.

For activity goals without sub-goals, a check is made at 610 to determine if the activity measured has met an activity performance goal over the last X minutes, where X is the activity period for that particular activity goal. If not, control moves to 602 and the activity is measured by activity monitor 102.

In the embodiment described with respect to FIG. 6, each activity goal with sub-goals includes a repetition requirement, wherein the repetition requirement sets a minimum number of times that a measured activity must meet the activity sub-goal over a given time period (such as a day, or a week). In one such embodiment, processor 106 maintains a repetition counter for each distinct sub-goal. That repetition counter is incremented each time its corresponding sub-goal is met. Then, the check at 610 to determine if the activity goal has been met includes comparing the contents of the repetition counter to the repetition requirement. In some embodiments, comparing the repetition counter to the repetition requirement includes notifying a user when the repetition requirement is met.

In some embodiments, each activity goal further includes a minimum rest period between activity periods. In some such embodiments, processor 106 notifies a user that the minimum rest period has expired.

In some embodiments, each activity goal further includes a minimum rest period between activity periods and a maximum rest period between activity periods.

In some embodiments, establishing an activity goal includes setting, as the maximum rest period, a maximum wait between activity periods, wherein the method further comprises determining if the maximum rest period has elapsed and, if the maximum rest period has elapsed, encouraging a user to engage in the activity.

Figure 7:
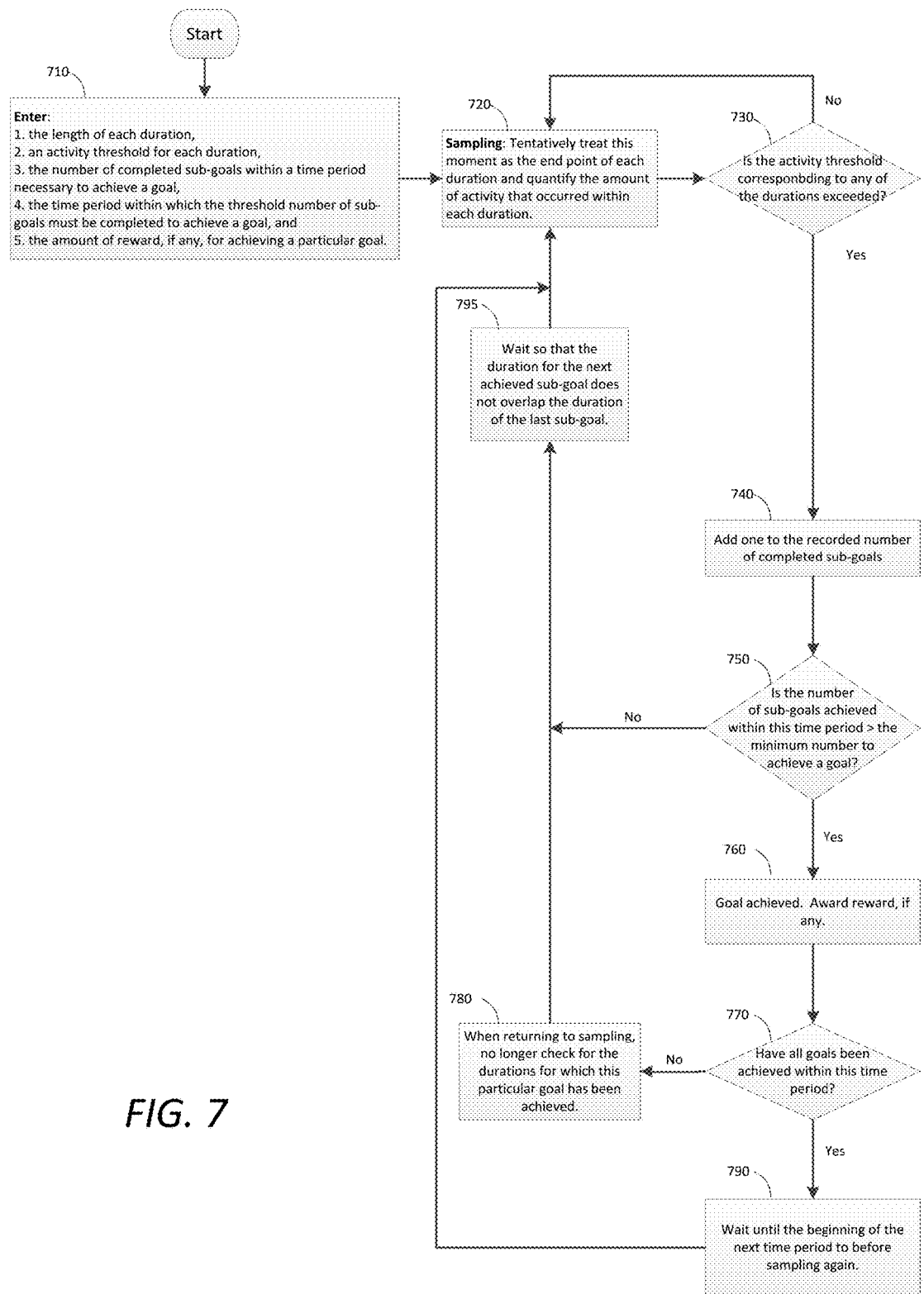
FIG. 7 illustrates a method for tracking and rewarding activity in the system of FIG. 1A.

Yet another method for tracking activity is shown in FIG. 7. In the example embodiment of FIG. 7, parameters of one or more activity goals are entered at 710, including, in some embodiments, the length of each duration, an activity threshold for each duration, the number of completed sub-goals within a time period necessary to achieve a goal, the time period within which the minimum number of sub-goals must be completed to achieve a goal, and the amount of reward, if any, for achieving a particular goal. At each moment, at 720, processor 106 quantifies the amount of activity within each of the entered durations that ends at that moment. Processor 106 then determines, at 730, whether any of the amounts of activity exceeds the activity threshold associated with that duration and, if so, adds one to the recorded number of completed sub-goals at 740. Processor 106 then determines, at 750, whether the new number of completed sub-goals is greater than the entered minimum. If so a goal is recorded and rewards, if any, are given at 760. Processor 106 then determines, at 770, whether all entered goals have been achieved within the designated time period and, if so, waits at 790 until the next time period to begin sampling. If not, control moves to 780 and system 100 returns to sampling, but no longer samples for the sub-goals associated with the achieved goal. Control then moves to 795 and processor 106 waits at 795 so that the duration for the next achieved sub-goal does not overlap the duration of the last instance of the same sub-goal. Control then moves to 820.

In some embodiments, the method of FIG. 7 is implemented as computer-executable instructions in which the following instructions are performed: Parameters are entered into system 100, including the length of each duration, an activity threshold for each duration, the number of completed sub-goals within a time period necessary to achieve a goal, the time period within which the minimum number of sub-goals must be completed to achieve a goal, and the amount of reward, if any, for achieving a particular goal. At each moment, the program causes a processor to quantify the amount of activity within each of the entered durations that ends at that moment). The program then causes a processor to determine whether any of the amounts of activity exceeds the activity threshold associated with that duration and, if so, adds one to the recorded number of completed sub-goals. The program then causes a processor to determine whether the new number of completed sub-goals is greater than the entered minimum. If so a goal is recorded and rewards, if any, are given. The program then causes processor 106 to determine whether all entered goals have been achieved and, if so, waits until the next time period to begin sampling. If not, it returns to sampling, but no longer samples for the sub-goals associated with the achieved goal. Before returning to sampling, the program causes a processor to wait so that the duration for the next achieved sub-goal does not overlap the duration of the last sub-goal.

Figure 8:
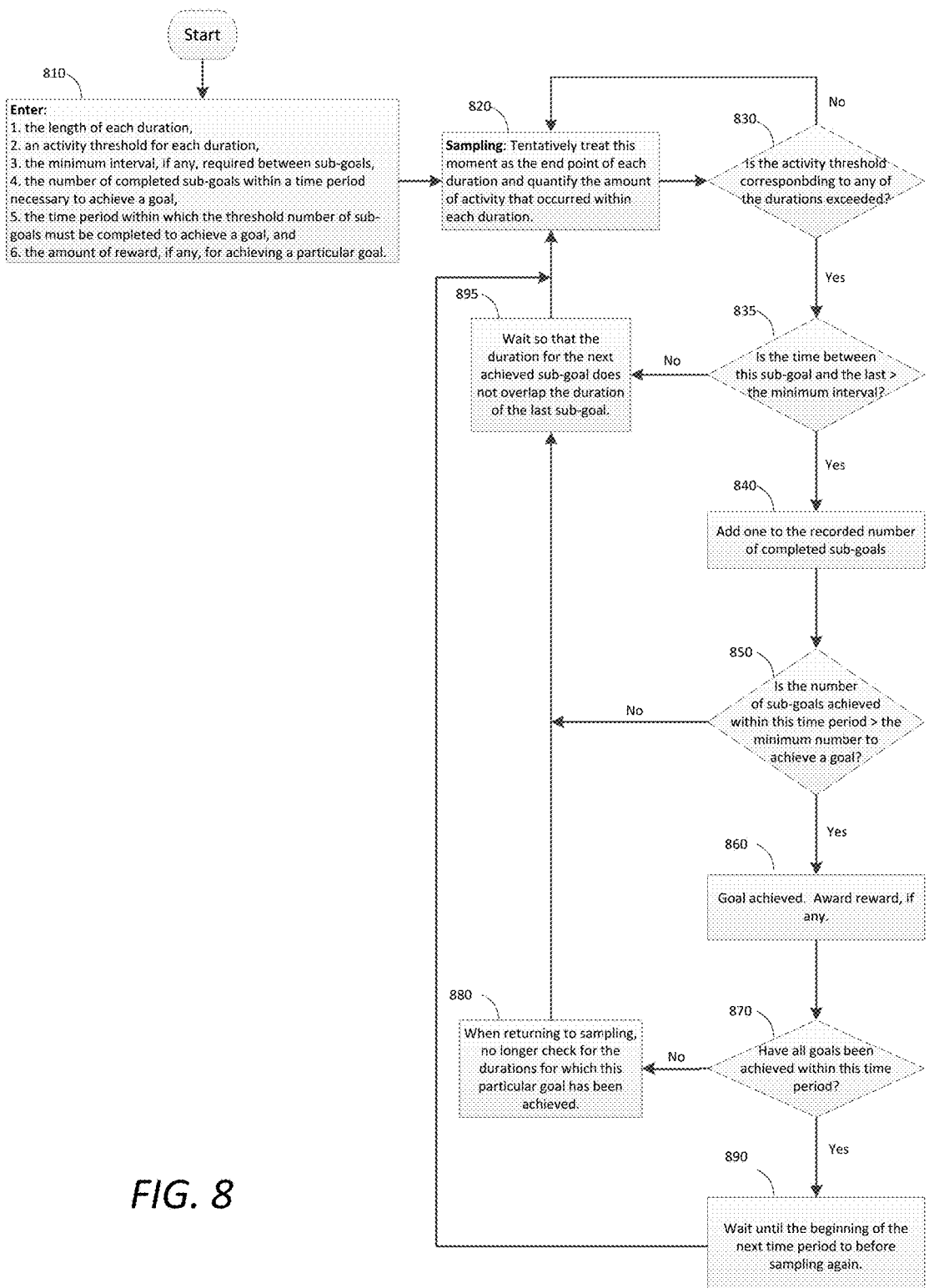
FIG. 8 illustrates another method for tracking and rewarding activity in the system of FIG. 1A.

Yet another method for tracking activity is shown in FIG. 8. In the example embodiment of FIG. 8, parameters of one or more activity goals are entered at 810, including in some embodiments, the length of each duration, an activity threshold for each duration, the minimum interval between instances of the same sub-goal, the number of completed sub-goals within a time period necessary to achieve a goal, the time period within which the minimum number of sub-goals must be completed to achieve a goal, and the amount of reward, if any, for achieving a particular goal. At each moment, at 820, processor 106 quantifies the amount of activity within each of the entered durations that ends at that moment. Processor 106 then determines, at 830, whether any of the amounts of activity exceeds the activity threshold associated with that duration and, if so, checks at 835 to see if the time between this sub-goal and a previous instance of the sub-goal is at least equal to the minimum interval defined for that sub-goal (if any). If not, control moves to 895. If, however, the time between this sub-goal and a previous instance of the sub-goal is at least equal to the minimum interval defined for that sub-goal (if any), processor 106 adds one to the recorded number of completed sub-goals at 840. Processor 106 then determines, at 850, whether the new number of completed sub-goals is greater than the entered minimum. If so a goal is recorded and rewards, if any, are given at 860. Processor 106 then determines, at 870, whether all entered goals have been achieved within the designated time period and, if so, waits at 890 until the next time period to begin sampling. If not, control moves to 880 and system 100 returns to sampling, but no longer samples for the sub-goals associated with the achieved goal. Control then moves to 895 and processor 106 waits at 895 so that the duration for the next achieved sub-goal does not overlap the duration of the last instance of the same sub-goal. Control then moves to 820.

In some embodiments, computer-executable instructions are assembled to implement the method of FIG. 8 in a similar manner as discussed for FIG. 7 above. A difference is that minimum intervals required between sub-goals are entered at 810 and applied at 835. In some such embodiments, before adding one to the recorded number of sub-goals, the program calculates the time interval since the last relevant sub-goal was achieved and does not add one to the recorded number of sub-goals if the interval is less than an entered minimum.

Figure 9A:
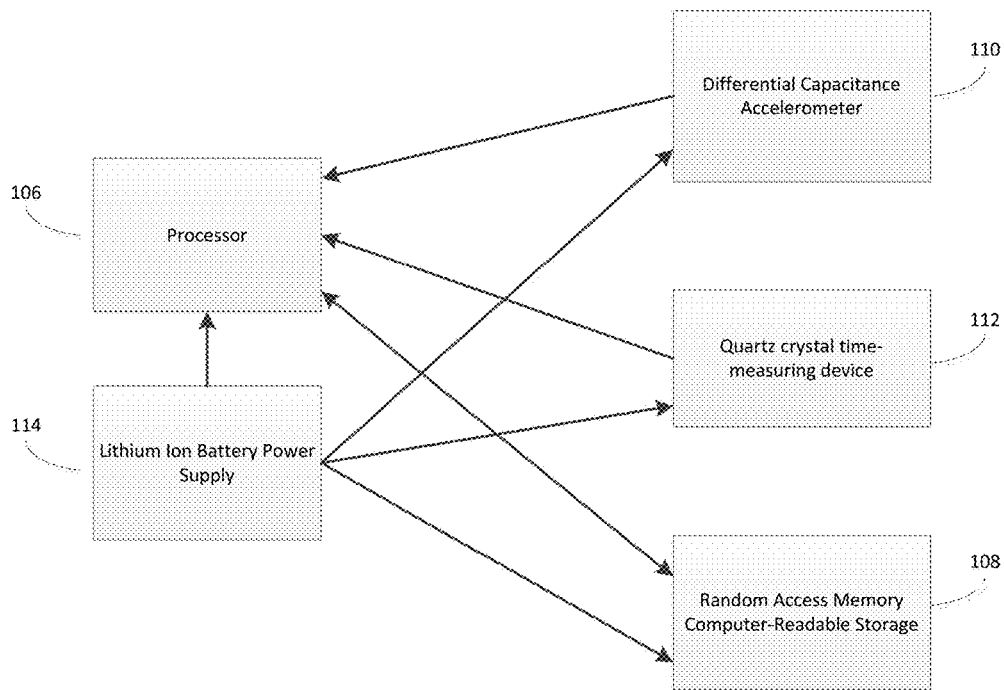
FIGS. 9A and 9B illustrate more detailed example embodiments of the system of FIG. 1A.
Figure 9B:
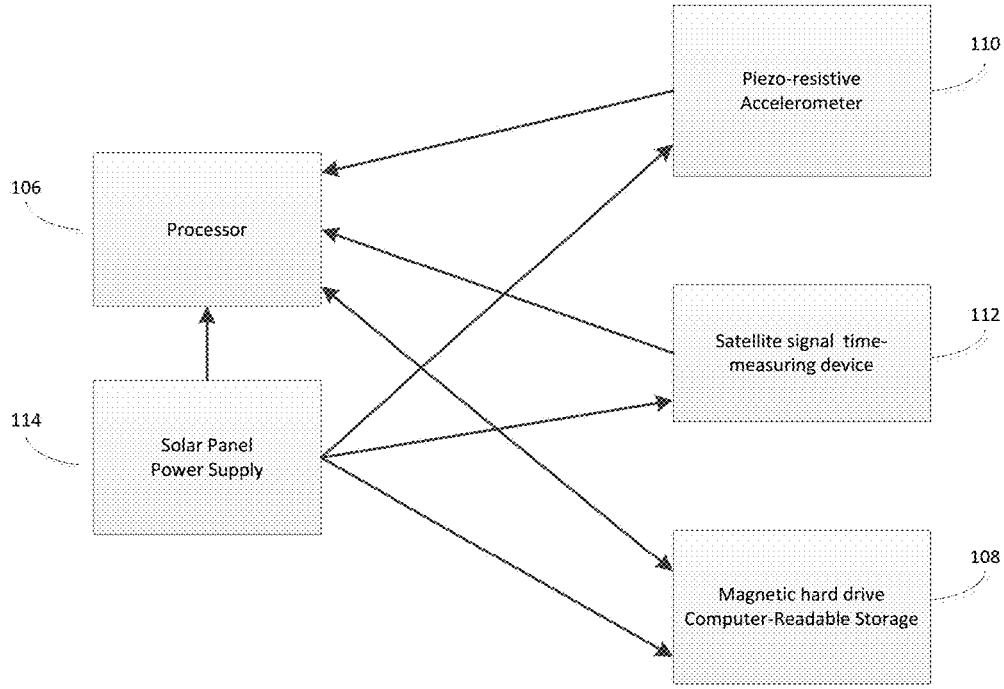

Other example embodiments of a system 100 for assessing physical activity are shown in FIGS. 9A and 9B. In FIGS. 9A and 9B, system 100 includes an accelerometer 110, a time measuring device 112, a processor 106, data storage 108 and power supply 114. Processor 106 is connected to accelerometer 110 and time measuring device 112 and receives activity data from accelerometer 110 and time measuring device 112.

In one embodiment, processor 106 receives information from both the accelerometer 110 and time-measuring device 112, which it combines to determine amounts of activity within durations. Processor 106 analyzes the data stream from accelerometer 110 to determine the completion of sub-goals and goals as described above.

In the example embodiment shown in FIG. 9A, accelerometer 110 measures acceleration via differential capacitance. Time-measuring device 112 measures time using a quartz crystal. Data storage 108 is a random access memory (RAM) chip while power supply 114 is a lithium ion battery. In one embodiment, processor 106 quantifies user activity as steps, which it counts by counting peaks in the accelerometer data that exceed a threshold magnitude. Using information from the time-measuring device 112 to determine the beginning and end of durations, processor 106 determines whether an activity threshold has been exceeded in a corresponding duration and, if so records the new number of achieved sub-goals on the RAM chip. Similarly, processor 106 determines whether a threshold number of sub-goals has been achieved within the specified time period.

In the example embodiment shown in FIG. 9B, accelerometer 110 measures acceleration via a piezo-resistor in a cantilever beam. Time-measuring device 112 measures time via satellite signals. Data storage 108 is a magnetic hard drive. Power supply 114 is a solar panel. In one embodiment, processor 106 quantifies user activity as calories, which it estimates by calculating the absolute value of the integral of the accelerometer signal. Using information from time-measuring device 112 to determine the beginning and end of durations, processor 106 determines whether an activity threshold has been exceeded in a corresponding duration and, if so records the new number of achieved sub-goals on the magnetic hard drive 108. Similarly, processor 106 determines whether a threshold number of subgoals has been achieved within the specified time period.

In one embodiment, system 100 assesses an individual's physical activity by counting the number of durations within which the individual exceeded associated activity thresholds, each instance of which is the achievement of a sub-goal, and determining whether the number of sub-goals achieved within a time period exceeds a minimum necessary to achieve a goal. In one such embodiment, a computing device performs the counting and determines if goals and sub-goals have been met by analyzing data from an accelerometer worn or carried by the individual.

In some embodiments, all durations are equal. In other embodiments, durations are not necessarily equal.

In some embodiments, system 100 includes a computer readable storage medium having data stored therein representing software executable by a computer, the software including instructions for the computer to count the number of durations within which the individual exceeded associated activity thresholds, each instance of which is the achievement of a sub-goal and determine whether the number of sub-goals achieved within a time period exceeds a minimum necessary to achieve a goal.

In the above description, methods of assessing an individual's physical activity are described. The methods act to determine whether an individual has completed predetermined activity goals. In some embodiments, a goal is completed when an individual has achieved a certain number of sub-goals within a time period. A sub-goal is achieved when the individual exceeds an activity threshold within an associated duration. In some embodiments, a minimum interval of time is required between sub-goals to ensure that frequency and intensity objectives are met. For this system allows an activity program to account for frequency and intensity as well as total amount of activity. In some embodiments, the physical activity assessment may be made by a device comprising an accelerometer and computing components. The computing components analyze the data stream received from accelerometer to determine the completion of sub-goals and goals.

The above detailed description includes references to the accompanying drawings, which form a part of the detailed description. The drawings show, by way of illustration, specific embodiments that may be practiced. These embodiments are also referred to herein as "examples." Such examples may include elements in addition to those shown or described. However, also contemplated are examples that include the elements shown or described. Moreover, also contemplate are examples using any combination or permutation of those elements shown or described (or one or more aspects thereof), either with respect to a particular example (or one or more aspects thereof), or with respect to other examples (or one or more aspects thereof) shown or described herein.

Publications, patents, and patent documents referred to in this document are incorporated by reference herein in their entirety, as though individually incorporated by reference. In the event of inconsistent usages between this document and those documents so incorporated by reference, the usage in the incorporated reference(s) are supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to suggest a numerical order for their objects.

The above description is intended to be illustrative, and not restrictive. For example, the above-described examples (or one or more aspects thereof) may be used in combination with others. Other embodiments may be used, such as by one of ordinary skill in the art upon reviewing the above description. The Abstract is to allow the reader to quickly ascertain the nature of the technical disclosure; it is submitted with the understanding that it will not be used to interpret or limit the scope or meaning of the claims. Also, in the above Detailed Description, various features may be grouped together to streamline the disclosure. However, the claims may not set forth every feature disclosed herein as embodiments may feature a subset of said features. Further, embodiments may include fewer features than those disclosed in a particular example. Thus, the following claims are hereby incorporated into the Detailed Description, with a claim standing on its own as a separate embodiment. The scope of the embodiments disclosed herein is to be determined with reference to the appended claims, along with the full scope of equivalents to which such claims are entitled.

What is claimed is:

1. A method, comprising:
receiving, by a computing device, at least one activity sensor signal produced by at least one accelerometer in response to physical movement of a person;
receiving, by the computing device, time information from a time measuring device;
for each of a plurality of predetermined durations:
quantifying an amount of activity indicated by the at least one activity sensor signal over a time period that is defined by the predetermined duration and measured by the received time information, and
comparing, by the computing device, the quantified activity amount to an activity threshold that is associated with the predetermined duration;
in response to a result of the comparing, for one of the plurality of predetermined durations, the respective quantified activity amount to the associated activity threshold, incrementing a number of performed repetitions of an activity sub-goal associated with the one of the plurality of predetermined durations;
determining, by the computing device, whether a first activity goal has been met based on the number of performed repetitions and a repetition requirement, the first activity goal comprising the activity sub-goal and a number of repetitions of the activity sub-goal; and
responsive to determining the first activity goal has been met, providing an indication of completion of the first activity goal.

2. The method of claim 1, wherein determining whether the first activity goal has been met includes incrementing a repetition counter each time the activity sub-goal has been met and comparing the repetition counter to the repetition requirement.

3. The method of claim 1, further comprising establishing the first activity goal comprising selecting a respective activity performance goal, a respective activity period, and a respective repetition requirement based on a moderate intensity activity for the person.

4. The method of claim 1, further comprising establishing the first activity goal comprising selecting, as a respective activity amount threshold, a challenging amount of activity for the person over a first predetermined duration of the plurality of predetermined durations.

5. The method of claim 1, wherein providing the indication of completion includes notifying a user if the repetition requirement has been met.

6. A non-transitory machine readable storage medium including processor-executable program code which, when executed by a processor, causes the processor to:
receive at least one activity sensor signal produced by at least one accelerometer in response to physical movement of a person;
receive time information from a time measuring device;
for each of a plurality of predetermined durations:
quantify an amount of activity indicated by the at least one activity sensor signal over a time period that is defined by the predetermined duration and measured by the received time information, and
compare the quantified activity amount to an activity threshold that is associated with the predetermined duration;
in response to a result of the comparing, for one of the plurality of predetermined durations, the respective quantified activity amount to the associated activity threshold, increment a number of performed repetitions of an activity sub-goal associated with the one of the plurality of predetermined durations;
determine whether a first activity goal has been met based on the number of performed repetitions and a repetition requirement, the first activity goal comprising the activity sub-goal and a number of repetitions of the activity sub-goal; and
responsive to a determination that the first activity goal has been met, provide an indication of completion of the first activity goal.

7. The non-transitory machine readable storage medium of claim 6, wherein the processor-executable program code which, when executed by the processor, further causes the processor to increment a repetition counter and compare the repetition counter to the repetition requirement.

8. The non-transitory machine readable storage medium of claim 7, wherein the processor-executable program code which, when executed by the processor, further causes the processor to notify a user when the repetition requirement is met.

9. The non-transitory machine readable storage medium of claim 6, wherein the activity goal further includes a minimum rest period between a first predetermined duration and a second predetermined duration of the plurality of predetermined durations.

10. The non-transitory machine readable storage medium of claim 9, wherein the processor-executable program code which, when executed by the processor, further causes the processor to notify a user that the minimum rest period has expired.

11. The non-transitory machine readable storage medium of claim 6, wherein the activity goal further includes a minimum rest period between a first predetermined duration and a second predetermined duration of the plurality of predetermined durations and a maximum rest period between the first predetermined duration and the second predetermined duration of the plurality of predetermined durations.

12. The non-transitory machine readable storage medium of claim 6, wherein the processor-executable program code which, when executed by the processor, further causes the processor to:
set, as a maximum rest period, a maximum wait between a first predetermined duration and a second predetermined duration of the plurality of predetermined durations,
determine if the maximum rest period has elapsed; and
if the maximum rest period has elapsed, encourage a user to engage in a user activity.

13. A method of assessing an individual's physical activity, comprising:
establishing one or more sub-goals, wherein each sub-goal includes an activity threshold and a predetermined duration;
counting a number of the one or more sub-goals met, the counting comprising:
receiving, by a computing device, at least one activity sensor signal produced by at least one accelerometer in response to physical movement of a person;
receiving, by the computing device, time information from a time measuring device;
for each of the one or more sub-goals:
quantify an amount of activity indicated by the at least one activity sensor signal over a time period that is defined by the predetermined duration and measured by the received time information, and
comparing, by the computing device, the quantified activity amount to the activity threshold of the sub-goal; and
in response to a result of the comparing, for one of the one or more sub-goals, the respective quantified activity amount to the activity threshold of the sub-goal, incrementing, by the computing device, a number of performed repetitions of the sub-goal;
determining, by the computing device, whether an activity goal is met, wherein the activity goal is met when an individual meets a number of sub-goals over a pre-defined time period; and
responsive to determining the activity goal has been met, providing an indication of completion of the activity goal.

14. A system for assessing physical activity comprising:
a processor;
an activity measurement device connected to the processor, wherein the activity measurement device comprises at least one accelerometer and is configured to transmit at least one activity sensor signal produced by the at least one accelerometer in response to physical movement of a person to the processor;
a time-measuring device connected to the processor, wherein the time-measuring device is configured to transmit time information to the processor; and
a computer-readable data storage device connected to the processor, wherein the processor is configured to execute processor-executable instructions to:
receive time information from the time-measuring device;
count a number of one or more sub-goals met, wherein each of the one or more sub-goals includes an activity threshold and a predetermined duration, and wherein the counting comprises:
for each of the one or more sub-goals:
quantify an amount of activity indicated by the at least one activity sensor signal over a time period that is defined by the predetermined duration and measured by the received time information; and
comparing the quantified activity amount to the activity threshold of the sub-goal; and in response to a result of the comparing, for one of the one or more sub-goals, the respective quantified activity amount to the activity threshold of the sub-goal, incrementing a number of performed repetitions of the sub-goal; and determine whether an activity goal is met, wherein the activity goal is met when an individual meets a selected number of sub-goals over a predefined time period.

15. The system of claim 14, wherein the activity measurement device includes a GPS sensor.

16. The system of claim 14, wherein the at least one accelerometer is selected from the group consisting of a uniaxial accelerometer, a biaxial accelerometer, and a triaxial accelerometer.

17. The system of claim 14, wherein the processor estimates steps by counting peaks in the at least one activity sensor signal that are greater than a specified magnitude.

18. The system of claim 17, wherein the processor estimates calories burned as a function of the at least one activity sensor signal, the at least one activity sensor signal received from the accelerometer.

19. The system of claim 14, wherein the time-measuring device is selected from the group consisting of an electronic quartz crystal clock, a pendulum clock, an atomic clock, a device receiving a satellite broadcast of time, and a device counting oscillations in an electrical current.

20. The system of claim 14, wherein the activity measurement device includes a heart rate monitor.

21. The system of claim 14, wherein the activity measurement device measures blood oxygen levels.

22. The method of claim 1, wherein receiving the at least one activity sensor signal; receiving the time information from the time measuring device; the quantifying the amount of activity and comparing the quantified activity amount for each of the plurality of predetermined durations; and the incrementing the number of performed repetitions are performed iteratively during a first time period.

* * * * *

UNITED STATES PATENT AND TRADEMARK OFFICE
CERTIFICATE OF CORRECTION

| | | |
|---|---|---|
| PATENT NO. | : 10,471,302 B1 | Page 1 of 1 |
| APPLICATION NO. | : 14/535895 | |
| DATED | : November 12, 2019 | |
| INVENTOR(S) | : Ehlert et al. | |

It is certified that error appears in the above-identified patent and that said Letters Patent is hereby corrected as shown below:

On the Title Page

"(73) Assignee: CAPSULE TECHNOLOGIES, INC.
San Diego, CA (US)"

Should read:
--(73) Assignee: UNITEDHEALTH GROUP INCORPORATED
Minnetonka, MN (US)--

Signed and Sealed this
Tenth Day of March, 2020

Andrei Iancu
*Director of the United States Patent and Trademark Office*